US012808804B2

(12) United States Patent
Ly et al.

(10) Patent No.: US 12,808,804 B2
(45) Date of Patent: Nov. 24, 2026

(54) ADJUSTABLE SLIDING PLATFORM FOR CELL CULTURE PLATE IMAGING

(71) Applicant: The Regents of the University of California, Oakland, CA (US)

(72) Inventors: Victoria Ly, Santa Cruz, CA (US); Mircea Teodorescu, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 883 days.

(21) Appl. No.: 17/738,262

(22) Filed: May 6, 2022

(65) Prior Publication Data

US 2022/0357278 A1 Nov. 10, 2022

Related U.S. Application Data

(60) Provisional application No. 63/242,449, filed on Sep. 9, 2021, provisional application No. 63/184,913, filed (Continued)

(51) Int. Cl.
*G01N 21/64* (2006.01)
*C12M 1/12* (2006.01)

(Continued)

(52) U.S. Cl.
CPC ......... *G01N 21/6458* (2013.01); *C12M 25/06* (2013.01); *G01N 21/6486* (2013.01);

(Continued)

(58) Field of Classification Search
CPC ........... G01N 21/6458; G01N 21/6486; G01N 2201/021; G01N 2201/062; G06T 7/571;

(Continued)

(56) References Cited

U.S. PATENT DOCUMENTS 3,466,514 A * 9/1969 Brunner ............... B23Q 1/4866 414/754
4,209,240 A * 6/1980 Sutherland .............. G03F 7/704 396/548

(Continued)

FOREIGN PATENT DOCUMENTS

CN 110104227 A * 8/2019 ............... B64G 1/66
CN 112261282 A * 1/2021 ........... H04N 23/698

(Continued)

OTHER PUBLICATIONS

Zhao, H., et al., "A screening platform for glioma growth and invasion using bioluminescence imaging", J. neurosurgery 111, 238-246 (2009).

(Continued)

*Primary Examiner* — Pinping Sun
*Assistant Examiner* — Andrew R Wright
(74) *Attorney, Agent, or Firm* — Carter, DeLuca & Farrell LLP

(57) ABSTRACT

An alignment platform for use with an imaging device includes an outer stage, an inner stage disposed within the outer stage and flexibly coupled to the outer stage, and a central frame disposed within the inner stage and flexibly coupled to the inner stage. The central frame is configured to support an object being imaged. The inner stage and the central frame are movable relative to the outer stage along a first axis and the central frame is movable relative to outer stage and the inner stage along a second axis that is perpendicular to the first axis.

20 Claims, 6 Drawing Sheets

Related U.S. Application Data on May 6, 2021, provisional application No. 63/184,915, filed on May 6, 2021.

(51) Int. Cl.
*G02B 21/36* (2006.01)
*G06T 7/571* (2017.01)
*H04N 5/265* (2006.01)
*H04N 23/62* (2023.01)
*H04N 23/66* (2023.01)
*H04N 23/90* (2023.01)

(52) U.S. Cl.
CPC ......... *G02B 21/365* (2013.01); *G02B 21/367* (2013.01); *G06T 7/571* (2017.01); *H04N 5/265* (2013.01); *H04N 23/62* (2023.01); *H04N 23/66* (2023.01); *H04N 23/90* (2023.01); *G01N 2201/021* (2013.01); *G01N 2201/062* (2013.01); *G06T 2207/10056* (2013.01); *G06T 2207/10148* (2013.01); *G06T 2207/30024* (2013.01); *G06T 2207/30072* (2013.01)

(58) Field of Classification Search
CPC . G06T 2207/10056; G06T 2207/10148; G06T 2207/30024; G06T 2207/30072; H04N 23/66; H04N 23/90; H04N 23/62; H04N 5/265; C12M 25/06; G02B 21/365; G02B 21/367
USPC .......................................................... 359/368
See application file for complete search history.

(56) References Cited

U.S. PATENT DOCUMENTS

| | | | | | |
|---|---|---|---|---|---|
| 4,476,492 A | * | 10/1984 | Muth | G12B 5/00 | 348/205 |
| 4,520,570 A | * | 6/1985 | Bednorz | B23Q 1/36 | 33/1 M |
| 5,297,130 A | * | 3/1994 | Tagawa | G01Q 10/04 | 310/317 |
| 5,684,856 A | * | 11/1997 | Itoh | G03F 7/70716 | 378/208 |
| 8,969,828 B2 | * | 3/2015 | Sakamoto | H01J 37/20 | 250/442.11 |
| 2002/0106912 A1 | * | 8/2002 | Gerbsch | H01R 13/24 | 439/66 |
| 2005/0259155 A1 | * | 11/2005 | Okada | H04N 23/66 | 348/207.99 |
| 2010/0231706 A1 | * | 9/2010 | Maguire, Jr. | G06F 3/011 | 348/121 |

FOREIGN PATENT DOCUMENTS

| | | | |
|---|---|---|---|
| JP | 6846065 B2 | * | 3/2021 |
| KR | 101957244 B1 | * | 5/2017 |

OTHER PUBLICATIONS

Almassalha, L. M. et al., "Label-free imaging of the native, living cellular nanoarchitecture using partial-wave spectroscopic microscopy", Proc. Natl. Acad. Sci. 113, E6372-E6381 (2016).
Martin, H. L. et al., "High-content, high-throughput screening for the identification of cytotoxic compounds based on cell morphology and cell proliferation markers", PloS one 9, e88338 (2014).
Dempsey, G. T. et al., "Cardiotoxicity screening with simultaneous optogenetic pacing, voltage imaging and calcium imaging", J. pharmacological toxicological methods 81, 240-250 (2016).
Honarnejad, K. et al., "Fret-based calcium imaging: a tool for high-throughput/content phenotypic drug screening in alzheimer disease", J. biomolecular screening 18, 1309-1320 (2013).
Park, J., et al., "Estimates of particulate matter inhalation doses during three-dimensional printing: How many particles can penetrate into our body?", Indoor air (2020).
Pearce, J. M., "Building research equipment with free, open-source hardware", Science 337, 1303-1304 (2012).
Mendoza-Gallegos, et al., "An affordable and portable thermocycler for real-time pcr made of 3d-printed parts and off-the-shelf electronics", Anal. chemistry 90, 5563-5568 (2018).
Kwon, H.-S. et al., "Performance of minipcr tm mini8, a portable thermal cycler", Anal. Sci. Technol. 29, 79-84 (2016).
Byagathvalli, G., et al., "A 3d-printed hand-powered centrifuge for molecular biology", PLoS biology 17, e3000251 (2019).
González-González, E., et al., "Portable and accurate diagnostics for covid-19: Combined use of the miniper thermocycler and a well-plate reader for sars-cov-2 virus detection", PloS one 15, e0237418 (2020).
Boguraev, A.-S. et al., Successful amplification of dna aboard the international space station:, NPJ microgravity 3, 1-4 (2017).
Hossain, Z. et al., "Interactive and scalable biology cloud experimentation for scientific inquiry and education", Nat. biotechnology 34, 1293-1298 (2016).
Klimaj, S. D., et al., "A high-throughput imaging and quantification pipeline for the evos imaging platform", Plos one 15, e0236397 (2020).
Ruckdäschel, S., "Time lapse imaging of spheroids-zencellowl incubator microscope", OMNI Life Sci. (2017).
Early, J. J. et al., "An automated high-resolution in vivo screen in zebrafish to identify chemical regulators of myelination", Elife 7, e35136 (2018).
Tsuji, N. et al., "Whole organism high content screening identifies stimulators of pancreatic beta-cell proliferation", PloS one 9, e104112 (2014).
Lemieux, G. A. et al., A whole-organism screen identifies new regulators of fat storage, Nat. chemical biology 7, 206-213 (2011).
Schreiber, K., et al., "A high-throughput chemical screen for resistance to pseudomonas syringae in *Arabidopsis*", The Plant J. 54, 522-531 (2008).
Renner, H. et al., "A fully automated high-throughput workflow for 3d-based chemical screening in human midbrain organoids", Elife 9, e52904 (2020).
Schuster, B. et al., "Automated microfluidic platform for dynamic and combinatorial drug screening of tumor organoids", Nat. communications 11, 1-12 (2020).
Willsey, H. R. et al., "The neurodevelopmental disorder risk gene dyrkla is required for ciliogenesis and control of brain size in xenopus embryos", Development 147 (2020).
Nieuwkoop, P. D. & Faber, J., "Normal table of xenopus laevis (daudin)", Copeia 1958, 65-65 (1958).
Thomson, J. A. et al., "Embryonic stem cell lines derived from human blastocysts", science 282, 1145-1147 (1998).
Specht, E. A., et al., "A critical and comparative review of fluorescent tools for live-cell imaging", Annu. review physiology 79, 93-117 (2017).
Godin, A. G., et al., "Super-resolution microscopy approaches for live cell imaging", Biophys. Journal 107, 1777-1784 (2014).
Miller, A. R. et al., "Portable, battery-operated, low-cost, bright field and fluorescence microscope", PloS one 5, e11890 (2010).
Selinummi, J. et al., "Bright field microscopy as an alternative to whole cell fluorescence in automated analysis of macrophage images", PloS one 4, e7497 (2009).
Hernández Vera, R., et al., "A modular and affordable time-lapse imaging and incubation system based on 3d-printed parts, a smartphone, and off-the-shelf electronics", PLoS One 11, e0167583 (2016).
Savas, J., et al., "Toward fully three-dimensional-printed miniaturized confocal imager", Opt. Eng. 57, 041402 (2018).
Wincott, M. B. et al. "Democratising" microscopi": a 3d printed automated XYZT fluorescence imaging system for teaching, outreach and fieldwork", bioRxiv (2020).
Yao, S., et al., "Automatic three-dimensional imaging for blastomere identification in early-stage embryos based on brightfield microscopy", Opt. Lasers Eng. 130, 106093 (2020).

(56) References Cited

OTHER PUBLICATIONS

Zamxaka, M., et al., "Microbiological and physico-chemical assessment of the quality of domestic water sources in selected rural communities of the eastern cape province, south africa", Water Sa 30, 333-340 (2004).
Ferreira, L. M. et al. "Effective participatory science education in a diverse latin american population", Palgrave Commun. 5, 63 (2019).
Giacomotto, J. & Ségalat, L. "High-throughput screening and small animal models, where are we?", Br. journal pharmacology 160, 204-216 (2010).
Willis, S., "The maker revolution", Computer 51, 62-65 (2018).
Barber, K. & Mostajo-Radji, "M. A. Youth networks' advances toward the sustainable development goals during the covid-19 pandemic", Front. Sociol. 5: 589539. doi: 10.3389/fsoc (2020).
Coakley, M. F. et al., "The nih 3d print exchange: a public resource for bioscientific and biomedical 3d prints", 3D printing additive manufacturing 1, 137-140 (2014).
Ambrose, B. et al., "Democratizing single-molecule fret: An open-source microscope for measuring precise distances and biomolecular dynamics", Biophys. J. 118, 614a (2020).
Gross, B. C., et al., "Evaluation of 3d printing and its potential impact on biotechnology and the chemical sciences", ACS Publ. (2014).
Baden, T. et al., "Open labware: 3-d printing your own lab equipment", PLoS biology 13, e1002086 (2015).
Alessandri, K. et al., "All-in-one 3d printed microscopy chamber for multidimensional imaging, the universlide", Sci. reports 7, 1-10 (2017).
Ventola, C. L., "Medical applications for 3d printing: current and projected uses", Pharm. Ther. 39, 704 (2014).
Beattie, R. J., et al., "Sparking curiosity through open-source platforms in education and science. Front", Educ. 5, 8 (2020).
Brown, J. W. et al., "Single-molecule detection on a portable 3d-printed microscope", Nat. communications 10, 1-7 (2019).
Khan, A., et al., "A low-cost 3d printed microfluidic bioreactor and imaging chamber for live-organoid imaging", Biomicrofluidics (2021).
Chagas, A. M., et al., "TheC 100 lab: A 3d-printable open-source platform for fluorescence microscopy, optogenetics, and accurate temperature control during behaviour of zebrafish, *Drosophila*, and *Caenorhabditis elegans*", PLoS biology 15, e2002702 (2017).
Kim, S. B. et al., "A mini-microscope for in situ monitoring of cells", Lab on a Chip 12, 3976-3982 (2012).
Diederich, B. et al., "A versatile and customizable low-cost 3d-printed open standard for microscopic imaging", Nat. communications 11, 1-9 (2020).
Wang, Z. et al., "A high-resolution minimicroscope system for wireless real-time monitoring", IEEE Transactions on Biomed. Eng. 65, 1524-1531 (2017).
Zhang, Y. S. et al., "A cost-effective fluorescence mini-microscope for biomedical applications", Lab on a Chip 15, 3661-3669 (2015).
Zhang, C., et al., "Open-source 3d-printable optics equipment", PloS one 8, e59840 (2013).
Collins, J. T. et al., "Robotic microscopy for everyone: the openflexure microscope", Biomed. Opt. Express 11, 2447-2460 (2020).
Cybulski, J. S., et al., "Foldscope: origami-based paper microscope", PloS one 9, e98781 (2014).
Kim, H. et al., "Ludusscope: accessible interactive smartphone microscopy for life-science education", PloS one 11, e0162602 (2016).
Aidukas, T., et al., "Low-cost, sub-micron resolution, wide-field computational microscopy using opensource hardware", Sci. reports 9, 1-12 (2019).
Bohm, A., "An inexpensive system for imaging the contents of multi-well plates", Acta Crystallogr. Sect. F: Struct. Biol. Commun. 74, 797-802 (2018).
Merces, G. O. et al., "The incubot: A 3d printer-based microscope for long-term live cell imaging within a tissue culture incubator", BioRxiv (2020).
Gürkan, G.& Gürkan, K., "Incu-stream 1.0: an open-hardware live-cell imaging system based on inverted bright-field microscopy and automated mechanical scanning for real-time and long-term imaging of microplates in incubator", IEEE Access 7, 58764-58779 (2019).
Kim, J., Henley,et al., "Incubator embedded cell culture imaging system (emsight) based on fourier ptychographic microscopy", Biomed. optics express 7, 3097-3110 (2016).
Uno, A. Arduino uno. online, (https://store. arduino. cc/usa/arduino-uno-rev3, diakses) 4 (2019).
Pi, R. Raspberry pi 4. online.(https://www. raspberrypi. org) (2015).
Beam, M. Makerbeam 10mm×10mm. online].(https://www.makerbeam.com/makerbeam/ (2021).
Fruit, A. Zero spy camera for raspberry pi zero. online.(https://www.adafruit.com/product/3508) (2015).
Goda, T. et al., "Genetic screens for mutations affecting development of xenopus tropicalis", PLoS Genet. 2, e91 (2006).
Borodinsky, L. N., "Xenopus laevis as a model organism for the study of spinal cord formation, development, function and regeneration", Front. neural circuits 11, 90 (2017).
Olmstead, A. W. et al., "Reproductive maturation of the tropical clawed frog: *Xenopus tropicalis*", Gen. comparative endocrinology 160, 117-123 (2009).
Hirsch, N., et al., "Xenopus, the next generation: X. tropicalis genetics and genomics", Dev. dynamics: an official publication Am. Assoc. Anat. 225, 422-433 (2002).
Mcnamara, S., et al., "Husbandry, general care, and transportation of xenopus laevis and xenopus tropicalis", Methods Mol Biol., 1-17 (Springer, 2018).
Khokha, M. K. et al., "Techniques and probes for the study of xenopus tropicalis development", Dev. dynamics: an official publication Am. Assoc. Anat. 225, 499-510 (2002).
Keller, R. & Sutherland, A., "Convergent extension in the amphibian, *Xenopus laevis*", In Current topics in developmental biology, vol. 136, 271-317 (Elsevier, 2020).
Baldwin, A., Kim, J. & Wallingford, J. B., "Global analysis of cell behavior and protein localization dynamics reveals region-specific functions for shroom3 and n-cadherin during neural tube closure", bioRxiv (2021).
Huebner, R. J. et al., "Cadherin clustering controls heterogeneous, asymmetric junction dynamics during vertebrate axis elongation", bioRxiv (2020).
Abe-Fukasawa, N., et al., "Novel 3d liquid cell culture method for anchorageindependent cell growth, cell imaging and automated drug screening", Sci. reports 8, 1-12 (2018).

* cited by examiner

ADJUSTABLE SLIDING PLATFORM FOR CELL CULTURE PLATE IMAGING

CROSS-REFERENCE TO RELATED APPLICATION

The present application claims the benefit of and priority to U.S. Provisional Application No. 63/184,913, filed on May 6, 2021; U.S. Provisional Application No. 63/184,915, filed on May 6, 2021; and U.S. Provisional Application No. 63/242,449, filed on Sep. 9, 2021. The entire disclosures of each of the foregoing applications are incorporated by reference herein.

GOVERNMENT LICENSE RIGHTS

This invention was made with government support under the National Institute of Mental Health of the National Institutes of Health under Award No. R01MH120295 and the National Science Foundation under Award No. NSF 2034037. The Government has certain rights in the invention.

BACKGROUND

Monitoring and handling live tissues and cell cultures as well as analyzing their secreted contents are essential tasks in experimental biology and biomedicine. Advances in microscopy have revolutionized biological studies, allowing scientists to perform observations of cellular processes and organisms' development and behaviors. Imaging has been pivotal to uncovering cellular mechanisms behind biological processes.

Longitudinal studies involve repeated observations, i.e., imaging, of samples over a desired period of time. Several options exist for performing longitudinal imaging of biological materials. These range from super-resolution microscopes that allow for imaging of individual biomolecules to conventional benchtop microscopes, which are common in academic research, industrial, and teaching laboratories.

When choosing between the different technologies for longitudinal live tissue imaging, several factors may be considered in the experimental design. These include the speed of the microscope being sufficient for the phenomenon being studied as well as microscope's ability to acquire images without damaging or disturbing the specimen, e.g., photobleaching. Additional factors include microscope's ability to image in the environmental conditions of the desired experiment, including temperature, light, and humidity. Furthermore, the resolution of the microscope being sufficient to view the phenomenon being studied is also an important factor. Conventional devices that are capable of simultaneous multi-well longitudinal tissue imaging are bulky and/or expensive. Thus, there is a need for an imaging device capable of meeting all of the criteria while being affordable and having a smaller-footprint than conventional imaging devices.

SUMMARY

The use of open-source technology, including 3D printers, laser cutters, and low-cost computer hardware, has democratized access to rapid prototyping tools and dramatically increased the repertoire of biomedical equipment available to laboratories around the world. Through rapid prototyping and the use of open-source platforms, technology can be replicated and quickly improved.

Typically, 3D manufacturing has two main approaches: additive (e.g., 3D printing) and subtractive (e.g., machining, laser cutting), with both methods requiring dedicated equipment. In the past some of these devices were limited to specialized manufacturing facilities. Over the past couple of decades, 3D manufacturing went through a revolution. Equipment such as 3D printers and computer numerical control (CNC) machinery has become affordable and ubiquitous in engineering laboratories. Research in the areas of labs-on-chip, optofluidics, microscopy, in combination with developments in consumer-oriented tools for makers, has the potential to democratize access to cell biology-based research. Laboratories are now able to more easily develop custom devices which can be shared with the greater research community as open-source projects. The present disclosure provides for an imaging device that is a culmination of these developments.

3D printer technology has been applied to several fields in biomedicine, including biotechnology bioengineering, and medical applications including fabrication of tissues and organs, casts, implants, and prostheses. Existing 3D printed microscopes range in complexity from simple low-cost systems with pre-loaded imaging modules to portable confocal microscopes capable of imaging individual molecules and even 3D printed microfluidic bioreactors. The majority of low-cost 3D printed microscopes are not intended for longitudinal imaging of simultaneous biological cultures (e.g., multi-well, multi-week biological experiments). They usually have a single imaging unit or perform confocal, and even light-sheet imaging. Other systems utilize a single camera attached to a gantry system to perform imaging of multiple experimental replicates (i.e., copies of a sample being analyzed). Few 3D-printed microscopes have been developed that perform multi-well imaging with medium throughput. Several biological applications exist that would greatly benefit from multi-well, multi-week simultaneous imaging, as this technology allows for concurrent interrogation of different experimental conditions and the inclusion of biological replicates. These include cell culture applications, in which 2D and 3D culture models can be tracked over multi-week periods, as well as developmental and behavioral biology experiments in which multi-week tracking could be performed on whole organisms.

The combination of 3D printed technology and open-source software has significantly increased the accessibility of academic and teaching laboratories to biomedical equipment. Thermocyclers, for example, were once an expensive commodity unattainable for many laboratories around the world. Now, low-cost thermocyclers have been shown to perform as well as high-end commercial equipment. Inexpensive thermocyclers can be used in a variety of previously unimaginable contexts, including conservation studies in the Amazon, diagnostics of Ebola, Zika and SARS-CoV-260,61, teaching high school students in the developing world and epigenetic studies onboard the International Space Station.

Simultaneous imaging of biological systems is crucial for drug discovery, genetic screening, and high-throughput phenotyping of biological processes and disease. This technique typically requires expensive multicamera and robotic equipment, making it inaccessible to most laboratories. While the need for a low-cost solution has long been appreciated, few solutions have been proposed. Currently, the low-cost solutions can be grouped in two categories: 1) those that use of gantry systems that move an individual camera through multiple wells, performing "semi-simultaneous" imaging or 2) those that use acquisition of large fields of view encompassing multiple wells, which results in limited resolution per well, followed by post-processing images. Neither of these solutions is optimal to perform true simultaneous imaging of biological replicates across multiple conditions. To overcome these limitations, the imaging device according to the present disclosure is configured to perform an automated image capture of a standard 24-well cell culture plate using 24 individual objectives.

Commercial electronic systems for simultaneous imaging of biological samples are typically designed to image cells plated in monolayers. Yet, significant attention has been given to longitudinal imaging-based screens using whole organisms. These have included zebrafish, worms, and plants. Many times, the results of the screens are based on single plane images or in maximal projections obtained from external microscopes. The imaging device according to the present disclosure overcomes these limitations and image along the z-axis. This is accomplished with fine adjustment by stepper motors that lift an elevator platform that holds all of the imaging units, each having an objective lens and a camera.

To date, few 3D printed microscopes are designed to function inside incubators. The presently disclosed imaging device may operate inside an incubator for up to 4 weeks. This allows the imaging device to operate with screens in 3D mammalian models including organoids. Since the imaging device according to the present disclosure may be used inside incubators, the imaging device may be used to perform longitudinal imaging of human cortical organoids and analyzing the behavior and movement of individual cells and other mammalian tissue.

Simultaneous longitudinal imaging across multiple conditions and replicates has been crucial for scientific studies aiming to understand biological processes and disease. Yet, imaging devices capable of accomplishing these tasks are economically unattainable for most academic and teaching laboratories around the world. The present disclosure provides a low-cost imaging device with a per well cost of less than $100 for simultaneous longitudinal biological imaging made primarily using off-the-shelf and 3D-printed materials.

The imaging device according to the present disclosure provides simultaneous multi-well imaging and may perform longitudinal brightfield z-stack imaging of any suitable cell culture plate, including conventional 24-well cell culture plates. The imaging device is also configured to capture 3D z-stack image data. The imaging device is configured to capture stacks of images and/or video at different focal layers, which is referred to as "z-plane stack" or "z-stack" due to the focal planes being stacked along a vertical, or z-axis. The imaging device is configured to simultaneously images in each one of a plurality (e.g., 24) of wells at multiple focal planes (the resolution of the "z-stack" can be remotely modified) at any suitable frequency, which may be impractical to perform manually. The imaging frequency may be from about 1 minute to about 24 hours, and images may be taken for any suitable period of time, which may be from 1 hour to about 30 weeks.

The imaging device is designed to illuminate the samples using one or more lighting sources from above and/or below the cell culture plate. Diffused illumination from below results in images that show contours and surface features. Illumination from above results in more visible detail and can show internal structures if the sample is sufficiently translucent. The flexibility of using different illumination techniques emulates commercial brightfield microscopes. The imaging device also includes an alignment platform which supports a cell culture plate holding biological samples during an experiment. The alignment platform may be moved along two axes (e.g., x axis and y axis) defining a horizontal plane.

The alignment platform is movable along a first and second axes (i.e., x axis and y axis) in either direction. The alignment platform includes a central frame holding the cell culture plate and two interconnected linear stages. The central frame is connected to the inner stage. The inner stage and the central frame are configured to translate relative to the outer stage along a second axis (e.g., y axis). The inner stage includes four rigid elements and a plurality of leaf springs (e.g., 4) connecting the central frame to the rigid elements of the inner stage surrounding the central frame. The outer stage is configured to translate along the first axis (e.g., x axis) and includes four rigid elements and additional leaf springs connecting the inner stage with the outer rigid elements. Two of the outer rigid elements are connected to the imaging device. While each stage can flex along one axis (e.g., x or y axes), together the two stages allow the alignment platform to move along both axes. Each stage may be actuated manually by two adjustment drive screws manually or in an automated manner using linear actuation mechanisms.

The imaging device further includes a plurality of imaging units, which may correspond to the number of wells of the cell culture plate, e.g., 24. The imaging units are coupled to an elevator platform configured to along one or more support columns. One or more stepper motors are configured to move the elevator platform vertically along a vertical axis (e.g., z axis) transverse to the horizontal plane of the alignment platform. The stepper motors may have a travel per step rate of from about 1 μm to about 10 μm to allow for focusing of specific biological features and collecting z-stack imaging. The imaging device may be controlled remotely via a remote computer, allowing for automatic imaging with minimal intervention from the investigator. Images are uploaded to the remote computer or server as they are captured allowing the user to view the results in near real time.

Many useful applications of the imaging device and derivatives thereof may also be envisioned. While the present disclosure provides a few exemplary uses of the imaging device disclosed herein, the versatility of the imaging device may be employed across various animal and cell models in different environmental conditions. The modular nature of the system allows for new features to be easily built and added, such as defined spectrum LED light sources and filters for fluorescent imaging may be added to enable longitudinal studies of the appearance and fate of defined sub populations of cells in a complex culture by taking advantage of genetically encoded fluorescent reporter proteins. Similarly, the use of fluorescent reporters or dyes that respond to dynamic cell states such as calcium sensors allow long-term imaging of cell activity. The imaging device disclosed herein provides increased accessibility and democratization of multi-well, multi-week simultaneous imaging experiments in diverse biological systems.

According to one embodiment of the present disclosure, an alignment platform for use with an imaging device is disclosed. The alignment platform includes an outer stage, an inner stage disposed within the outer stage and flexibly coupled to the outer stage, and a central frame disposed within the inner stage and flexibly coupled to the inner stage. The central frame is configured to support an object being imaged. The inner stage and the central frame are movable relative to the outer stage along a first axis and the central frame is movable relative to outer stage and the inner stage along a second axis that is perpendicular to the first axis.

Implementations of the above embodiment may include one or more of the following features. According to one aspect of the above embodiment, the outer stage, the inner stage, and the central frame may have a substantially rectangular frame. The central frame may be coupled to the inner stage via a first plurality of flexible elements and the inner stage may be coupled to the outer stage via a second plurality of flexible elements. The inner stage may include a first pair of opposing rigid elements that are parallel to the first axis and a second pair of opposing rigid elements that are parallel to the second axis. The first plurality of flexible elements may be coupled to the central frame and each rigid element of the second pair of opposing rigid elements of the inner stage. The outer stage may include a first pair of opposing rigid elements that are parallel to the first axis and a second pair of opposing rigid elements that are parallel to the second axis. The second plurality of flexible elements may be coupled to each rigid element of the first pair of opposing rigid elements of the inner stage and an adjacent rigid element of the first pair of opposing rigid elements of the outer stage.

The first plurality of flexible elements and the second plurality of flexible elements may be leaf springs. Each flexible member of the first plurality of flexible elements is parallel to the first axis and is deflectable in a direction parallel to the second axis. Each of flexible members of the second plurality of flexible elements is parallel to the second axis and is deflectable in a direction parallel to the first axis. Each of the outer stage, the inner stage, the central frame, the first plurality of flexible elements, and the second plurality of flexible elements are formed as a single piece using a 3D printer.

The alignment platform may further include a first drive screw configured to move the inner stage and the central frame relative to the outer stage along the first axis and a second drive screw configured to move the central frame relative to the outer stage along the second axis.

According to another embodiment of the present disclosure, an imaging device is disclosed. The imaging device includes an alignment platform having an outer stage, an inner stage disposed within the outer stage and flexibly coupled to the outer stage, and a central frame disposed within the inner stage and flexibly coupled to the inner stage. The central frame is configured to support an object being imaged. The inner stage and the central frame are movable relative to the outer stage along a first axis and the central frame is movable relative to outer stage and the inner stage along a second axis that is perpendicular to the first axis. The device also includes an imaging assembly configured to image the object.

Implementations of the above embodiment may include one or more of the following features. According to one aspect of the above embodiment, the imaging device may also include a first drive screw configured to move the inner stage and the central frame relative to the outer stage along the first axis, and a second drive screw configured to move the central frame relative to the outer stage along the second axis. The imaging device may also include a first actuator coupled to the first drive screw and configured to move the first drive screw longitudinally parallel to the first axis and a second actuator coupled to the second drive screw and configured to move the second drive screw longitudinally parallel to the second axis. The imaging device may also include a controller configured to command each of the first actuator and the second actuator to move to a set distance. Each of the outer stage, the inner stage, and the central frame has a substantially rectangular frame.

The central frame may be coupled to the inner stage via a first plurality of flexible elements and the inner stage may be coupled to the outer stage via a second plurality of flexible elements. Each flexible member of the first plurality of flexible elements is parallel to the first axis and is deflectable in a direction parallel to the second axis. Each of flexible members of the second plurality of flexible elements is parallel to the second axis and is deflectable in a direction parallel to the first axis.

BRIEF DESCRIPTION OF DRAWINGS

Various embodiments of the present disclosure are described herein below with reference to the figures wherein.

DETAILED DESCRIPTION

Figure 1:
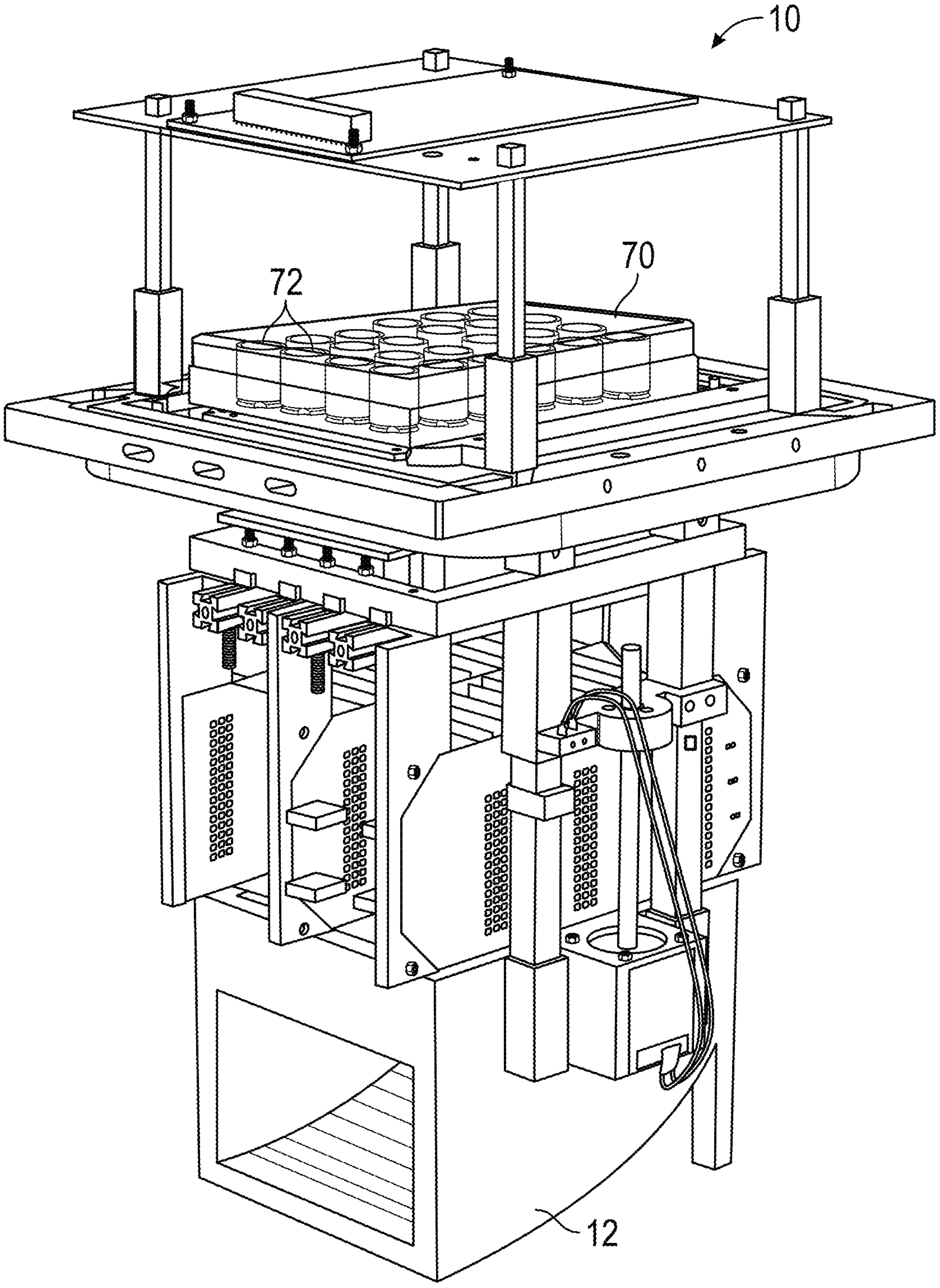
FIG. 1 is a photograph of an imaging device holding a cell culture plate according to one embodiment of the present disclosure.
Figure 2:
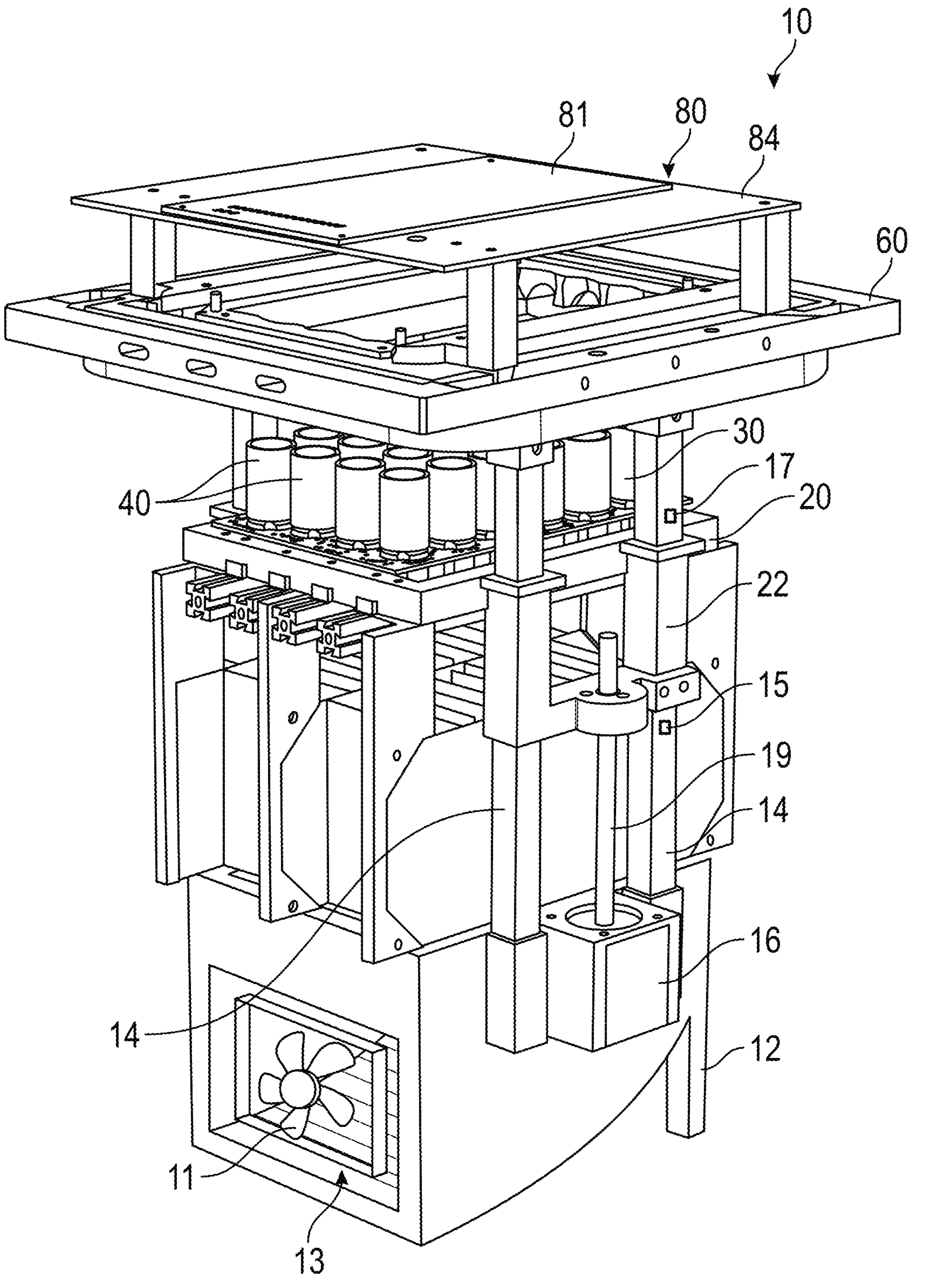
FIG. 2 is a perspective view of the imaging device FIG. 1.

FIGS. 1 and 2 show an imaging device 10 having a base 12 with one or more columns 14 extending vertically from the base 12. The base 12 may include an intake 13 and a fan 11 disposed in communication with the intake 13 for heat dissipation. The base 12 and/or the footprint of the imaging device 10 may be from about 100 $cm^2$ to about 500 $cm^2$ providing for portability of the imaging device 10. In embodiments, the imaging device 10 may have a width and depth of from about 30 cm to about 70 cm and may have a height from about 30 cm to about 80 cm.

The columns 14 may be formed from any suitable rigid material, such as metal. The columns 14 may be formed from aluminum extrusions, such as those available from MakerBeam of Utrecht, Netherlands. The columns 14 may have a square cross-section (e.g., 10 mm×10 mm) and have a length of about 200 mm. The columns 14 are used as guides for an elevator platform 20, which is movable vertically along the columns 14 by one or more actuators 16. The actuators 16 may be electric stepper motors configured to move and hold any discrete position for precisely moving the elevator platform 20. The discrete position, i.e., distance traveled per step, may be from about from about 1 μm to about 10 μm. The elevator platform 20 includes a plurality of sleeves 22, each of which is configured to slidably fit around each of columns 14. Each of the actuators 16 includes a drive shaft 19, which when actuated, moves the elevator platform 20 along a vertical axis. Various mechanical interfaces that convert rotational motion output by the actuators 16 and/or the drive shaft 19 into linear motion of the elevator platform 20 may be used, and include, but are not limited to, worm gears, bevel gears, and the like. Mechanical interfaces may be disposed at the elevator platform 20 and/or the actuators 16.

The elevator platform 20 supports an imaging assembly 30 having a plurality of imaging units 40 disposed in a matrix, i.e., a plurality of imaging arrays of imaging units 40. The imaging assembly 30 includes a plurality of imaging units 40. Each imaging array may have any suitable number of imaging units 40, which may be from 1 to 10, depending on the number of cells being imaged.

Each of the imaging units 40 includes a camera body 42 housing a camera 44 and a lens assembly 46. The camera 44 may be any digital image capturing device, such as Raspberry Pi Camera Module v2, and may have any suitable resolution, e.g., 5 MP and pixel pitch of about 1.4 μm×1.4 μm. The lens assembly 46 may have an optical format of 1/2.5" and a focal length of 16 mm, such as Arducam 1/2.5" M12 mount 16 mm focal length camera lens. The lens assembly 46 may have any number of lenses and may have any desired focal length for imaging the samples "S".

Figure 3:
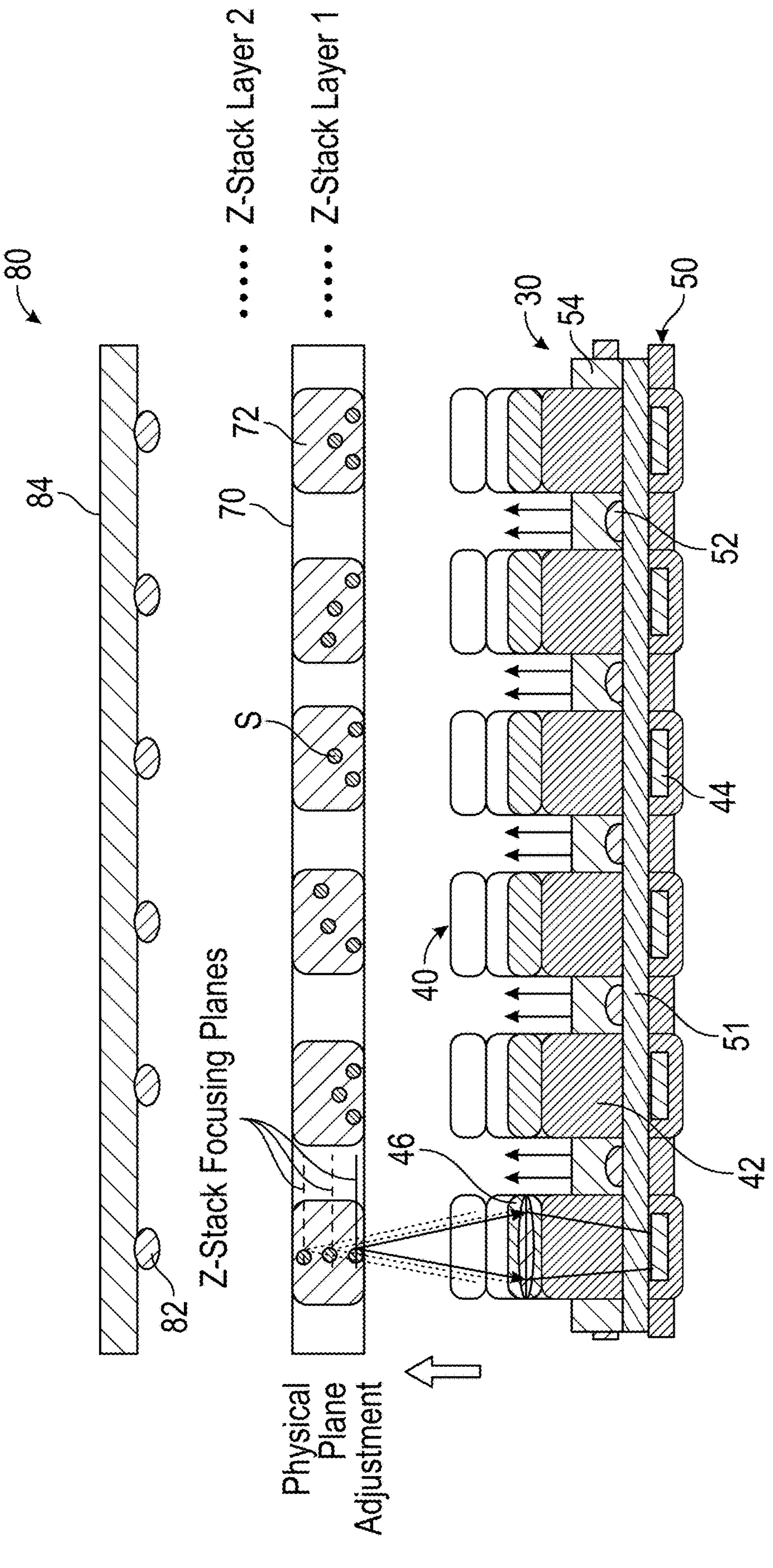
FIG. 3 is a schematic diagram of an array of imaging assemblies and the cell culture plate according to one embodiment of the present disclosure.

With reference to FIG. 3, the imaging assembly 30 also includes a first illumination assembly 50 having a substrate 51, which may be a printed circuit board (PCB) or any other suitable rigid substrate. The PCB may be a 1.6 mm FR4 two-layer PCB. The first illumination assembly 50 includes a plurality of light emitting devices 52, which may be light emitting diodes (LEDs) or the like. The LEDs 52 are disposed on the substrate 51 and are located between the imaging units 40 allowing for forward lighting of the samples "S". The first illumination assembly 50 also includes a light diffusing layer 54, which may be formed from any suitable transparent material, such as acrylics, and the like. The light diffusing layer 54 may be used to encase the LEDs 52 on the substrate 51. The light diffusing layer 54 may be machined from a sheet of acrylic, which may have a thickness from about 5 mm to about 10 mm, using CNC machines, such as Nomad883 Pro.

With reference to FIGS. 1 and 2, the imaging device 10 also includes an alignment platform 60, which is securely coupled to the columns 14. The alignment platform 60 is configured to support a cell culture plate 70 having a plurality of wells 72. The alignment platform 60 acts as an alignment platform for the cell culture plate 70 relative to the imaging assembly 30. The alignment platform 60 is disposed above the elevator platform 20 such that the imaging assembly 30 is configured to illuminate and image the samples "S" held in the wells 72 of the cell culture plate 70.

Structural components of the imaging device 10 may be formed using any additive techniques, such as 3D printing using MK3S Prusa 3D printer (PRUSA) or any other suitable 3D printer. Polylactic acid (PLA) such as Prusa Slic3r (PRUSA) or any other suitable polymers may be used. In embodiments, other 3D printable materials may be used, such as metals. The parts may be created with computer aided design (CAD) using any suitable application, such as Fusion 360 and AutoCAD (Autodesk). In embodiments, the base 12, the elevator platform 20, the alignment platform 60, and other structural components may be formed using 3D printers. The components may be printed using infill settings from about 80% to about 100% with resolution of about 0.15 mm or higher. In embodiments, supports may be used during printing.

The cell culture plate 70 includes 24 wells 72. In embodiments, the cell culture plate 70 may have any number of wells 72, which may be from 1 to 96 wells, including 1, 2, 4, 8, 24, 48, or 96 wells. The cell culture plate 70 may have any suitable dimensions, including width, length, and height. The wells 72 may also be of any desired dimension, e.g., diameter, depth, and spacing between neighboring wells 72. The design of the imaging device 10 is based on the type of the cell culture plate 70 being used since the number of the imaging units 40, spacing between the imaging units 40, and configuration of the imaging assembly 30 depends on the number, spacing, and configuration of the cell culture plate 70. Thus, in an exemplary embodiment where the cell culture plate 70 includes 24 wells 72, the imaging units 40 are arranged in the same configuration, i.e., in a 4×6 matrix (e.g., 4 rows and 6 columns), such that each of the wells 72 is individually imaged by a corresponding imaging unit 40.

With reference to FIGS. 2 and 3, the imaging device 10 further includes a second illumination assembly 80 disposed above the alignment platform 60. The second illumination assembly 80 is securely coupled to the alignment platform 60. The second illumination assembly 80 is configured to provide backlighting of the samples "S" held in the wells 72 of the cell culture plate 70 and allowing for brightfield imaging. The second illumination assembly 80 may include a substrate 81 (FIG. 2), which may be a PCB or any other suitable rigid substrate. The second illumination assembly 80 includes a plurality of LEDs 82, which may be light emitting diodes or the like. The LEDs 82 are disposed on the substrate 81 in the same pattern as the imaging units 40 such that each of the LEDs 82, the wells 72, and the imaging units 40 are vertically aligned, i.e., arranged along the same vertical axis. The second illumination assembly 80 also includes a light diffusing layer 84, which may be formed from any suitable transparent material, such as acrylics, and the like. The light diffusing layer 84 may be used to encase the LEDs 82 on the substrate 81.

In embodiments, the LEDs 52 and 82 may be output light at any desired wavelength and spectrum. The LEDs 52 and 82 may output white broad-spectrum light. The LEDs 52 and 82 may be MEIHUA white LEDs with a brightness of from about 228 MCD to about 450 MCD, and the brightness can be adjusted through a potentiometer. The LEDs 52 and 82 may also be NCD063W3 Chip Light Emitting Diodes.

The LEDs 52 and 82 may be defined spectrum LEDs configured to output infrared or ultraviolet light to enable fluorescent imaging of samples "S". Such light sources may be used to perform longitudinal studies of the appearance and fate of defined sub populations of cells in a complex culture having genetically encoded fluorescent reporter proteins.

Imaging of the samples "S" held within the wells 72 of the cell culture plate 70 occurs by initially adjusting each of the wells 72 to be in alignment with each of the imaging units 40, i.e., along x and y axis. In addition, the vertical distance of the elevator platform 20 is also adjusted, i.e., along z axis, to focus on a desired z-axis focal plane. This is particularly useful in samples "S" having one or more objects (e.g., embryos) disposed in different vertical (i.e., focal) planes. Transition between different focal planes is accomplished by adjusting the actuators 16 to move the elevator platform 20 by precise amounts, which may be from about 0.1 mm to about 1 mm.

Figure 4:
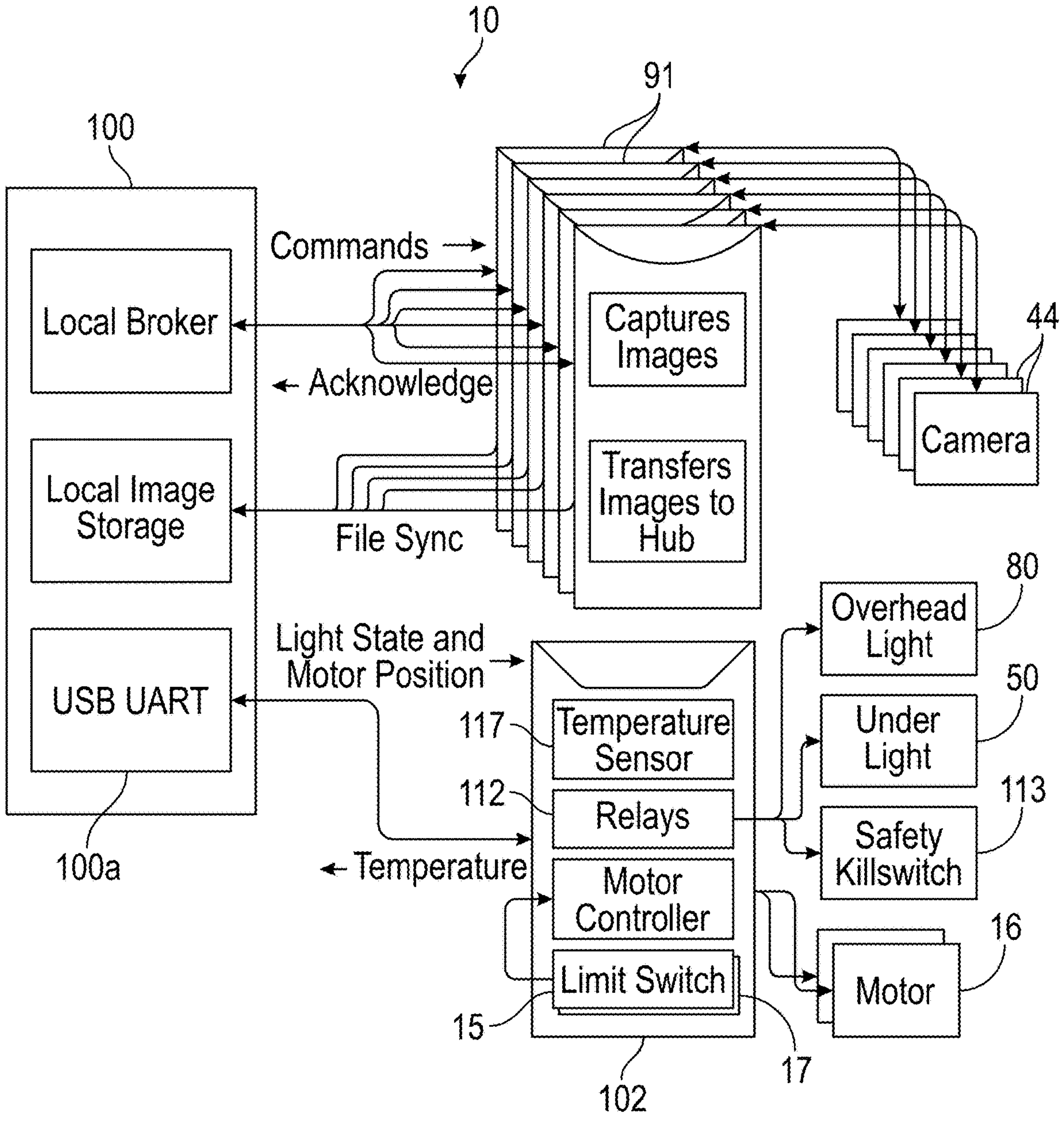
FIG. 4 is a schematic diagram of a computer architecture of the imaging device according to one embodiment of the present disclosure.

With reference to FIG. 4, the imaging device 10 includes a plurality of camera controllers 91, each of which is coupled to one of the cameras 44 using a ribbon cable or any other suitable connector. The camera controllers 91 may be any suitable computing device, such as Raspberry Pi Zero W. The camera controllers 91 are coupled to a hub controller 100, which may be a Raspberry Pi 4, or any other suitable computing device. The hub controller 100 communicates with each of the camera controllers 91 using any suitable wired or wireless communication interface.

The hub controller 100 is configured to command the cameras 44 to capture images, store captured images, process images, tag images, and the like. The images may be stored in any suitable file format, such as JPEG, RAW, etc. The hub controller 100 is also coupled to a hardware controller 102 using any suitable interface 100*a*, such as USB. The hardware controller 102 may be any suitable computing device, such as an Arduino Uno and is configured to control movement of the actuators 16. In particular, the hub controller 100 is configured to output a movement command based on a desired distance movement and the hardware controller 102 is configured to translate the movement command into a number of discrete steps for moving the actuators 16 to achieve the desired movement command. The hub controller 100 is also coupled to one or more relays 112, which are configured to toggle the first illumination assembly 50 and the second illumination assembly 80 individually as well as shut off power to the entire imaging device 10 in the event of an emergency via a kill switch 113.

The hub controller 100 is also coupled to a lower limit switch 15 and an upper limit switch 17 (FIG. 2) engageable by the elevator platform 20 upon reaching lower and upper limits, respectively. In addition, the hub controller 100 is further coupled to a temperature and/or humidity sensor 117. Sensor data from the sensor 117 is provided to the hub controller 100. In the event humidity or temperature is outside operating limits, the hub controller 100 shuts down the imaging device 10, thereby protecting the imaging device 10 and the samples.

The sensor 117 may be used in conjunction with the fan 11 to control the temperature of the imaging device 10. In embodiments, the hub controller 100 may control the fan 11 (e.g., turning the fan 11 on or off, adjusting the speed, etc.) based on the temperature and/or humidity measurement data from the sensor 117. This is particularly useful when using the imaging device 10 with temperature sensitive samples and/or environment. In particular, the imaging device 10 may be used in temperature and/or humidity-controlled $CO_2$ incubators. If the sensor 117 senses that temperature is excessive, then the hub controller 100 can shut down the imaging device 10 to prevent the incubator for overheating and preserving the cell culture samples "S" or increase the circulation of the fan 11.

The imaging process includes placing the cell culture plate 70 on the alignment platform 60. This may also include adjusting the position of the cell culture plate 70 on the alignment platform 60 along the x and y axes to align the wells 72 with the imaging units 40. The hub controller 100 may then take images of the samples "S" held by the alignment platform 60 to confirm that the samples "S" are adequately illuminated and are in focus. The hub controller 100 may set light color and intensity of the first illumination assembly 50 and the second illumination assembly 80. The hub controller 100 also adjusts the vertical position of the elevator platform 20 to achieve desired focus of the images. Once these settings are finalized, the hub controller 100 may be programmed to set the duration of the longitudinal study, which may be from about 1 hour to about 30 weeks. The hub controller 100 also configures the frequency of the images being taken during the study period. After each set of pictures, the imaging unit returns to the lowest ("park") position, which is determined by activation of the lower limit switch 15 by the elevator platform 20.

Figure 5:
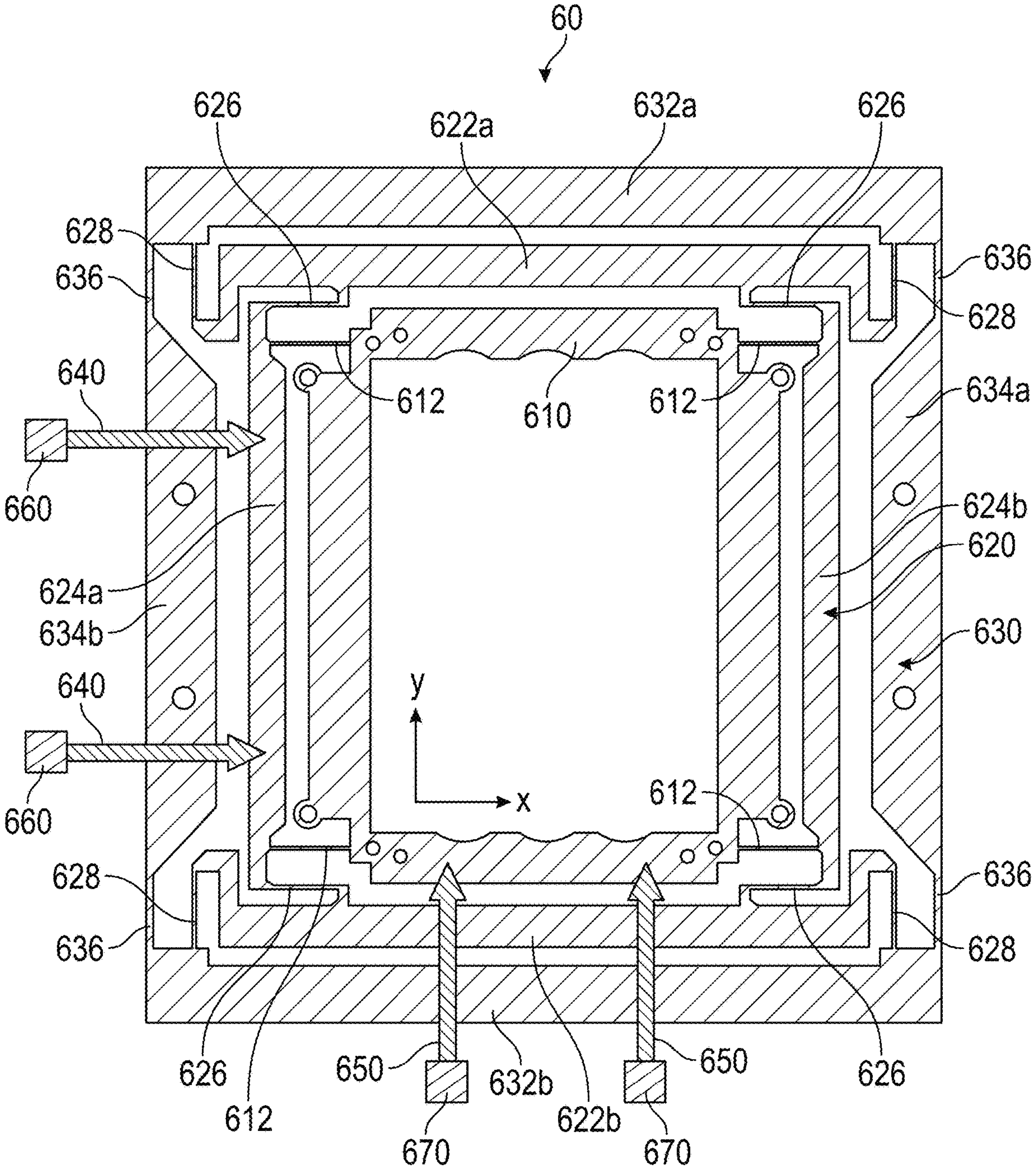
FIG. 5 is a plan view of a cell culture plate alignment platform according to one embodiment of the present disclosure.

With reference to FIG. 5, the alignment platform 60 includes a central frame 610 and two interconnected linear stages, namely, an inner stage 620 and an outer stage 630, all of which are disposed on the same plane defined by the first and second axes (i.e., x and y). The central frame 610 is configured to secure the cell culture plate 70. Each of the central frame 610 and the inner and outer stages 620 and 630 may have a substantially rectangular shape. The central frame 610 is disposed within the inner stage 620, which is turn, disposed within the outer stage 630. The central frame 610 is flexibly coupled to the inner stage 620 via a plurality of flexible members 612, which may be leaf springs. Similarly, the inner stage 620 is flexibly coupled to the outer stage 630 using flexible members 628.

The inner stage 620 includes two pairs of rigid elements 622*a* and 622*b* and 624*a* and 624*b* forming four sides of a rectangle defined by the inner stage 620. Each of the rigid elements 622*a* and 622*b* is disposed along an axis parallel to the first axis and is coupled to the second pair of the rigid elements 624*a* and 624*b* via flexible members 626. Each of the rigid elements 624*a* and 624*b* is disposed along an axis parallel to the second axis, i.e., perpendicular to the first axis. The flexible members 626 are disposed at opposing end portions of each of the rigid elements 622*a*, 622*b*, 624*a*, 624*b*. In addition, the central frame 610 is coupled to the second pair of rigid elements 624*a*, 624*b* using four flexible members 612, each of which couples one corner portion of the central frame 610 to each of the end portions of the rigid elements 622*a*, 622*b*. All of the flexible members 612 and 626 interconnecting the central frame 610 and the inner stage 620 are parallel to a first axis (i.e., x axis) such that the flexible members 612 and 626 are configured to deflect along a second axis (i.e., y axis) in a direction perpendicular to the first axis.

The outer stage 630 also includes two pairs of rigid elements 632*a* and 632*b* and 634*a* and 634*b* defining a rectangle. The rigid elements 632*a* and 632*b* are disposed along an axis that is parallel to the first axis and the rigid elements 634*a* and 634*b* are disposed along an axis that is parallel to the second axis. The first pair of the rigid elements 622*a* and 622*b* of the inner stage 620 is coupled to the first pair of rigid elements 632*a* and 632*b* of the outer stage 630 via flexible elements 628. The flexible elements 628 extend from the end portions of the rigid elements 624*a* and 624*b* and terminate or couple at end portions of the rigid elements 632*a* and 632*b*, which themselves are also coupled via supports 636 to the second pair of rigid elements 634*a* and 634*b*. The supports 636 may also be flexible elements and extend from the end portions of the rigid elements 634*a* and 634*b* and terminate or couple to the end portions of the rigid elements 632*a* and 632*b*. Each of the rigid elements 634*a* and 634*b* is securely coupled to the imaging device 10. This may be done by using fasteners, adhesive, or any other attachment means to secure the rigid elements 634*a* and 634*b* the columns 14 or any other housing or frame portion of the imaging device 10. The flexible members 628 interconnecting the inner stage 620 and the outer stage 630 are parallel to the second axis (i.e., y axis) such that the flexible members 628 are configured to deflect along first axis (i.e., x axis) in a direction transverse to the first axis.

The alignment platform 60 may be manufactured using 3D printing as a single piece using PLA or any other suitable polymer or metal. This technique allows for formation of interconnected flexible and rigid elements, which in turn, enable sliding or moving of certain components, i.e., central frame 610 and/or the inner stage 620, relative to other components of the alignment platform 60. It is envisioned that other manufacturing techniques may be used to make the alignment platform 60, such as 3D printing individual components and attaching them to each other using adhesive and/or fasteners. In further embodiments, the flexible and rigid elements may be formed from any other materials, such as metals, wood, etc. that provide similar material properties that enable the functionality of the alignment platform 60.

The alignment platform 60 also includes first and second adjustment drive screws 640 and 650 for adjusting or aligning the position of the central frame 610 relative to the inner stage 620 and/or outer stage 630, respectively. While a pair of adjustment drive screws 640 and 650 are shown, in embodiments, one adjustment drive screw per side may be used.

To adjust the central frame 610 along the first axis (i.e., x axis), the first adjustment drive screws 640 are moved longitudinally parallel to the first axis. While FIG. 5 shows the first adjustment drive screws 640 contacting the rigid element 624*a*, the first adjustment drive screws 640 may be disposed on the opposite side to contact the rigid element 624*b*. The first adjustment drive screws 640 pass through the rigid element 634*a* (e.g., through an opening) without shifting the outer stage 630. The first adjustment drive screws 640 contact the inner stage 620, and particular, the rigid elements 624*a*, which is parallel to the second axis.

As first adjustment drive screws 640 are moved parallel the first axis, the rigid element 624*a* is moved in the same direction. The flexible bands 612 and 626 resist bending since they are disposed parallel to the same axis as the direction of the force imparted by first adjustment drive screws 640. However, since the flexible bands 628 are disposed parallel to the second axis (i.e., y axis), the flexible bands 628 deflect in the same direction as first adjustment drive screws 640, thereby shifting the inner stage 620 and the central frame 610 in the same direction. This allows for movement of the central frame 610 and the cell culture plate 70 parallel to the first axis.

To adjust the central frame 610 parallel to the second axis (i.e., y axis), the second adjustment drive screws 650 are moved longitudinally parallel to the second axis. While FIG. 5 shows the second adjustment drive screws 650 passing through the rigid elements 622*b* and 632*b*, the first adjustment drive screws 640 may be disposed on the opposite side, to pass through the rigid elements 622*a* and 632*a*. The second adjustment drive screws 650 pass through the rigid element 632*b* of the outer stage 630 (e.g., through an opening) without shifting the outer stage 630. The second adjustment drive screws 650 also pass through the rigid element 622*b* of the inner stage 620 (e.g., through an opening) without shifting the inner stage 620.

The second adjustment drive screws 650 contact the central frame 610. As second adjustment drive screws 650 are moved parallel to the second axis, the central frame 610 is moved in the same direction. The flexible bands 628 resist bending since they are disposed parallel to the same axis as the direction of the force imparted by second adjustment drive screws 650. However, since the flexible bands 612 and 626 are disposed parallel the first axis (i.e., x axis), the flexible bands 628 deflect in the same direction as second adjustment drive screws 650, thereby shifting only the central frame 610 in the same direction. This allows for movement of the central frame 610 and the cell culture plate 70 parallel to the second axis.

The first and second adjustment drive screws 640 and 650 may be adjusted by manually turning each of first and second adjustment drive screws 640 and 650 or automatically by using actuators 660 and 670 coupled to first and second adjustment drive screws 640 and 650, respectively, as described further below with respect to FIG. 6. The actuators 660 and 670, may be similar to the actuators 16 and may be electric stepper motors configured to move and hold any discrete position for precisely moving the central frame 610. The actuators 660 and 670 are coupled to the hardware controller 102, which provides movement commands thereto.

Figure 6:
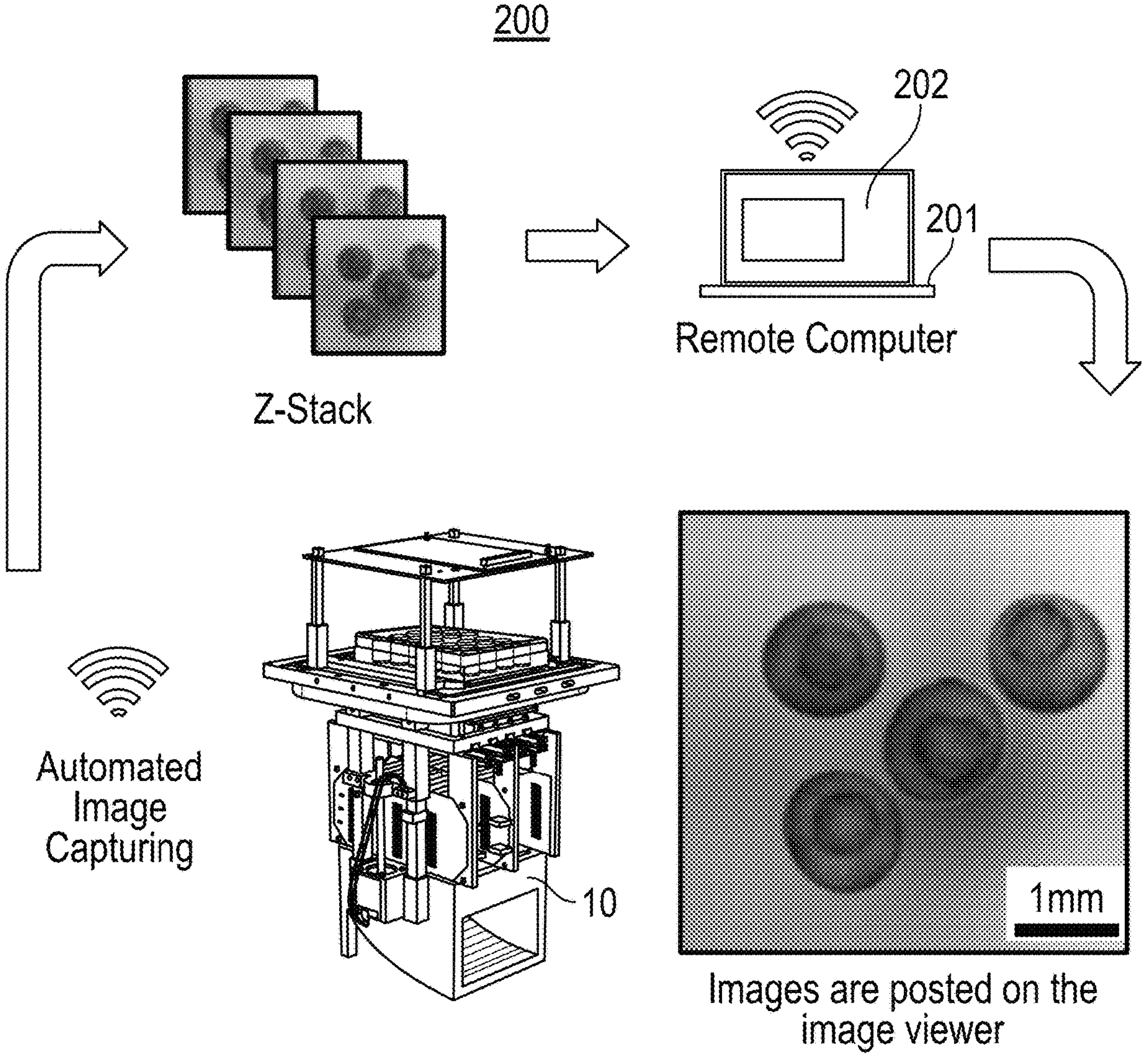
FIG. 6 is a schematic diagram of an imaging system including the imaging device and a computer according to one embodiment of the present disclosure.

With reference to FIG. 6, an imaging system 200 is shown, which includes the imaging device 10 in communication with a computer 201, which may be a laptop, a desktop, a server, or a virtualized computer, in communication with the imaging device 10. The computer 201 may be coupled to the imaging device 10 using a wired interface, such as USB, or any communication network based on wired or wireless communication protocols. The term "network," whether plural or singular, as used herein, denotes a data network, including, but not limited to, the Internet, Intranet, a wide area network, or a local area networks, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 122.15.4-2003 standard for wireless personal area networks (WPANs)).

As noted above, the hub controller 100 may include any suitable wireless or wired interface for connecting to the computer 201. The images may then be transferred to the computer 201, where the images can be viewed and/or processed with minimal intervention. The computer 201 may also include a display 202 allowing for viewing of the images. In addition, the computer 201 may be used to input experiment and operating parameters for the imaging device 10 via the hub controller 100.

The computer 201 may execute a control console application for controlling the imaging device 10. In embodiments, the control console may be embodied as a web page and the computer 201 may be configured to execute a web browser or any other application for accessing the web page. As used herein, the term "application" may include a computer program designed to perform functions, tasks, or activities for the benefit of a user. Application may refer to, for example, software running locally or remotely, as a standalone program or in a web browser, or other software which would be understood by one skilled in the art to be an application. An application may run on a controller, or on a user device, including, for example, a mobile device, a personal computer, or a server system.

The computer 201 allows the user to enter various imaging experiment parameters including, but not limited to, name or identifier of the experiment, stack size—which defines number of focal planes at which images are taken, step size—which defines the distance between each focal plane, step offset—which defines the distance for the first image of the stack, interval—time between images, duration of the imaging experiment, etc. The computer 201 may also allow for entering text-based camera command parameters, such as white balance and exposure settings. In addition, drop down menus may be used to adjust presets for lighting and other corresponding camera presets.

In addition to imaging parameters, the computer 201 may also be used for adjustment and alignment of the cell culture plate 70 to the imaging assembly 40 on the x-y plane. For manual or automated adjustment, the computer 201 may be used to provide a real-time view of each of the cameras 44 allowing for movement of the central frame 610 as described above using the first and second adjustment drive screws 640 and 650. For automated adjustment, the user may input movement commands (e.g., in inches or millimeters) to move the central frame 610 by a precise amount until each of the wells 72 is centrally disposed within the field of view of each of the corresponding cameras 44. The movement commands are transmitted to the hub controller 100, which is coupled to the actuators 660 and 670 through the hardware controller 102. Separate movement commands are provided to each of the actuators 660 and 670 to move the first and second adjustment drive screws 640 and 650 a set distance.

In further embodiments, the computer 201 may execute an image processing algorithm to determine whether each of the wells 72 is centrally aligned with the cameras 44. If a misalignment is determined, the computer 201 may further determine an amount (i.e., distance away from center) of misalignment for each of the axes (i.e., x and y). The amount of misalignment may then be used to command each of the actuators 660 and 670 to move the central frame 610 to correct for misalignment.

The computing devices (e.g., camera controllers 91, hub controller 100, computer 201, etc.) according to the present disclosure may be a virtualized computer, containerized application (e.g., Docker), or any other computing platform having a processor operably connected to a memory, which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

It will be appreciated that of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims. Unless specifically recited in a claim, steps or components according to claims should not be implied or imported from the specification or any other claims as to any particular order, number, position, size, shape, angle, or material.

What is claimed is:

1. An alignment platform for use with an imaging device, the alignment platform comprising:

an outer stage including a first pair of outer opposing rigid elements that are parallel to a first axis and a second pair of outer opposing rigid elements that are parallel to a second axis, wherein the second axis is perpendicular to the first axis;

an inner stage disposed within the outer stage and flexibly coupled to the outer stage, the inner stage including a first pair of inner opposing rigid elements and a second pair of inner opposing rigid elements;

a central frame disposed within the inner stage and flexibly coupled to the inner stage, the central frame configured to support an object being imaged, wherein the inner stage and the central frame are movable relative to the outer stage along the first axis and the central frame is movable relative to outer stage along the second axis;

a first plurality of flexible elements coupling the central frame to the inner stage;

a second plurality of flexible elements coupling the inner stage to the outer stage;

a third plurality of flexible elements coupling the first pair of inner opposing rigid elements and the second pair of inner opposing rigid elements, wherein the first pair of inner opposing rigid elements are movable relative to the second pair of inner opposing rigid elements, and wherein each flexible member of the third plurality of flexible elements is parallel to each flexible member of the first plurality of flexible elements;

a fourth plurality of flexible elements coupling the first pair of outer opposing rigid elements and the second pair of outer opposing rigid elements; and a first drive screw configured to move the inner stage and the central frame relative to the outer stage along the first axis, wherein the first drive screw passes through an outer rigid element of the first pair of outer opposing rigid elements, and wherein the first drive screw is configured to contact the inner stage without moving the outer stage.

2. The alignment platform according to claim 1, wherein each of the outer stage, the inner stage, and the central frame has a substantially rectangular frame.

3. The alignment platform according to claim 1, wherein the first pair of inner opposing rigid elements are parallel to the first axis and the second pair of inner opposing rigid elements are parallel to the second axis.

4. The alignment platform according to claim 3, wherein the first plurality of flexible elements is coupled to the central frame and each rigid element of the second pair of inner opposing rigid elements of the inner stage.

5. The alignment platform according to claim 1, wherein the second plurality of flexible elements is coupled to each rigid element of the first pair of inner opposing rigid elements of the inner stage and an adjacent rigid element of the first pair of outer opposing rigid elements of the outer stage.

6. The alignment platform according to claim 1, wherein the first plurality of flexible elements and the second plurality of flexible elements are leaf springs.

7. The alignment platform according to claim 1, wherein each flexible member of the first plurality of flexible elements is parallel to the first axis and is deflectable in a direction parallel to the second axis.

8. The alignment platform according to claim 1, wherein each flexible member of the second plurality of flexible elements is parallel to the second axis and is deflectable in a direction parallel to the first axis.

9. The alignment platform according to claim 1, wherein each of the outer stage, the inner stage, the central frame, the first plurality of flexible elements, and the second plurality of flexible elements are formed as a single piece using a 3D printer.

10. The alignment platform according to claim 1, further comprising:

a second drive screw configured to move the central frame relative to the outer stage along the second axis.

11. An imaging device comprising:

an alignment platform including:

an outer stage including a first pair of outer opposing rigid elements that are parallel to a first axis and a second pair of outer opposing rigid elements that are parallel to a second axis, wherein the second axis is perpendicular to the first axis;

an inner stage disposed within the outer stage and flexibly coupled to the outer stage, the inner stage including a first pair of inner opposing rigid elements and a second pair of inner opposing rigid elements;

a central frame disposed within the inner stage and flexibly coupled to the inner stage, the central frame configured to support an object being imaged, wherein the inner stage and the central frame are movable relative to the outer stage along the first axis and the central frame is movable relative to outer stage along the second axis;

a first plurality of flexible elements coupling the central frame to the inner stage;

a second plurality of flexible elements coupling the inner stage to the outer stage;

a third plurality of flexible elements coupling the first pair of inner opposing rigid elements and the second pair of inner opposing rigid elements, wherein the first pair of inner opposing rigid elements are movable relative to the second pair of inner opposing rigid elements, and wherein each flexible member of the third plurality of flexible elements is parallel to each flexible member of the first plurality of flexible elements;

a fourth plurality of flexible elements coupling the first pair of outer opposing rigid elements and the second pair of outer opposing rigid elements; and a first drive screw configured to move the inner stage and the central frame relative to the outer stage along the first axis, wherein the first drive screw passes through an outer rigid element of the first pair of outer opposing rigid elements, and wherein the first drive screw is configured to contact the inner stage without moving the outer stage; and an imaging assembly configured to image the object.

12. The imaging device according to claim 11, further comprising:

a second drive screw configured to move the central frame relative to the outer stage along the second axis.

13. The imaging device according to claim 12, further comprising:

a first actuator coupled to the first drive screw and configured to move the first drive screw longitudinally parallel to the first axis; and a second actuator coupled to the second drive screw and configured to move the second drive screw longitudinally parallel to the second axis.

14. The imaging device according to claim 13, further comprising:

a controller configured to command each of the first actuator and the second actuator to move to a first set distance and a second set distance, respectively.

15. The imaging device according to claim 11, wherein each of the outer stage, the inner stage, and the central frame has a substantially rectangular frame.

16. The imaging device according to claim 11, wherein each flexible member of the first plurality of flexible elements is parallel to the first axis and is deflectable in a direction parallel to the second axis.

17. The imaging device according to claim 11, wherein each flexible member of the second plurality of flexible elements is parallel to the second axis and is deflectable in a direction parallel to the first axis.

18. The alignment platform according to claim 10, wherein the second drive screw passes through an outer rigid element of the second pair of outer opposing rigid elements, wherein the second drive screw passes through an inner rigid element of the second pair of inner opposing rigid elements, and wherein the second drive screw is configured to contact the central frame without moving the outer stage and the inner stage.

19. The imaging device according to claim 12, wherein the second drive screw passes through an outer rigid element of the second pair of outer opposing rigid elements, wherein the second drive screw passes through an inner rigid element of the second pair of inner opposing rigid elements, and wherein the second drive screw is configured to contact the central frame without moving the outer stage and the inner stage.

20. The alignment platform according to claim 1, wherein each flexible member of the fourth plurality of flexible elements is parallel to each flexible member of the second plurality of flexible elements.

* * * * *